(12) United States Patent
Luo et al.

(10) Patent No.: US 11,649,406 B2
(45) Date of Patent: May 16, 2023

(54) METHOD AND SYSTEM FOR SEPARATING LIGHT HYDROCARBONS

(71) Applicants: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

(72) Inventors: Shujuan Luo, Beijing (CN); Dongfeng Li, Beijing (CN); Mingsen Zhang, Beijing (CN); Lihua Liao, Beijing (CN); Yan Li, Beijing (CN); Zhixin Liu, Beijing (CN); Chunfang Li, Beijing (CN); Jun Tian, Beijing (CN)

(73) Assignees: CHINA PETROLEUM & CHEMICAL CORPORATION, Beijing (CN); BEIJING RESEARCH INSTITUTE OF CHEMICAL INDUSTRY, CHINA PETROLEUM & CHEMICAL CORPORATION, Beijing (CN)

(*) Notice: Subject to any disclaimer, the term of this patent is extended or adjusted under 35 U.S.C. 154(b) by 33 days.

(21) Appl. No.: 17/283,606

(22) PCT Filed: Sep. 29, 2019

(86) PCT No.: PCT/CN2019/109082
§ 371 (c)(1),
(2) Date: Apr. 8, 2021

(87) PCT Pub. No.: WO2020/073853
PCT Pub. Date: Apr. 16, 2020

(65) Prior Publication Data
US 2021/0348071 A1     Nov. 11, 2021

(30) Foreign Application Priority Data

Oct. 8, 2018 (CN) .......................... 201811168501.5
Oct. 8, 2018 (CN) .......................... 201811169248.5

(51) Int. Cl.
*C10G 55/04* (2006.01)
*C10G 31/06* (2006.01)
(Continued)

(52) U.S. Cl.
CPC ................ *C10G 55/04* (2013.01); *C07C 7/11* (2013.01); *C10G 9/002* (2013.01); *C10G 25/11* (2013.01);
(Continued)

(58) Field of Classification Search
CPC ........ C10G 55/04; C10G 9/002; C10G 25/11; C10G 31/06; C10G 53/08; C07C 7/11; C07C 7/00; C07C 2/82–84
See application file for complete search history.

(56) References Cited

U.S. PATENT DOCUMENTS

2015/0246856 A1* 9/2015 Schmigalle .............. C10G 9/36
585/324
2015/0368167 A1 12/2015 Weinberger et al.

FOREIGN PATENT DOCUMENTS

CN        102093157        6/2011
CN        104781217        7/2015
(Continued)

OTHER PUBLICATIONS

English machine translation of CN 104557387, obtained from Search (Year: 2017).*
(Continued)

*Primary Examiner* — Renee Robinson
(74) *Attorney, Agent, or Firm* — Finnegan Henderson Farabow Garrett & Dunner LLP

(57) ABSTRACT

A method and system for separating light hydrocarbons are disclosed, wherein the method comprises compression, cooling, absorption, desorption, rectification, cracking, and recycling cracked gas to the compression step.

36 Claims, 4 Drawing Sheets

(51) Int. Cl.
 *C10G 53/08* (2006.01)
 *C10G 9/00* (2006.01)
 *C10G 25/11* (2006.01)
 *C07C 7/11* (2006.01)
 *C07C 2/84* (2006.01)

(52) U.S. Cl.
 CPC .......... *C10G 31/06* (2013.01); *C10G 53/08* (2013.01); *C07C 2/84* (2013.01); *C10G 2300/4081* (2013.01); *C10G 2400/20* (2013.01); *C10G 2400/28* (2013.01)

(56) References Cited

FOREIGN PATENT DOCUMENTS

| CN | 104557387 | * | 2/2017 | ............... C07C 7/11 |
|----|-----------|---|--------|---------------------------|
| CN | 201710006765.X | | 6/2017 | |
| CN | 109678636 | | 4/2019 | |
| CN | 110041156 | | 7/2019 | |
| WO | WO2015105911 | | 7/2015 | |

OTHER PUBLICATIONS

English machine translation of CN 109678636, obtained from Search (Year: 2019).*

International Search Report for International Application No. PCT/CN2019/109082, dated Dec. 27, 2019.

* cited by examiner

METHOD AND SYSTEM FOR SEPARATING LIGHT HYDROCARBONS

Cross-Reference to Related Applications

This application is a national stage filing under 35 U.S.C. § 371 of International Application No. PCT/CN2019/109082, filed Sep. 29, 2019, which claims the priority to and benefits of Chinese Patent Application No. 201811168501.5, filed Oct. 8, 2018, and Chinese Patent Application No. 201811169248.5, filed Oct. 8, 2018, which are incorporated herein by reference in their entireties.

FIELD OF THE INVENTION

The present invention belongs to the field of chemical industry, and in particular relates to a method and a system for separating low hydrocarbons.

BACKGROUND OF THE INVENTION

Ethylene is the most important basic organic chemical feedstock. For a long time, ethylene has been produced dependently by a route of cracking petroleum, and the environmental pollution and other problems caused by this route become increasingly serious. As the price of crude oil continuously increases, the price of cracking feedstock for ethylene increases and the cracking feedstock is in short supply. Facing this situation, countries in the world adjust the energy utilization structure and constantly look for new routes for producing ethylene. In 2010, the United States achieved a breakthrough in the field of shale gas. A large amount of methane that was difficult to extract was extracted, and the chemical utilization of methane drew a great attention in the industry. Therefore, the research on the oxidative coupling of methane to ethylene and ethane has become a hotspot worldwide.

The oxidative coupling of methane to ethylene is to convert methane to ethylene under the action of a catalyst. The reaction products are relatively complex, and mainly include methane, ethylene, ethane, CO, $CO_2$, $O_2$, and etc. Many methods for separating ethylene from the reaction mixture have been developed in the art.

US20150368167 discloses a method for separating OCM reaction product. Three product streams, i.e. a C2-rich stream, a nitrogen-rich stream, and a methane-rich stream can be obtained through a separating unit. The OCM reaction product is firstly separated in a first separating tower to obtain the C2-rich stream and a methane-nitrogen stream, and then the methane-nitrogen stream is separated in a second separating tower to obtain the nitrogen-rich stream and the methane-rich stream. A low-temperature rectification is utilized in the separating methods, and thus the temperature of the entire separating unit is very low. The tower top temperature of the first separating tower is low to about −162° C., and the tower top temperature of the second separating tower is low to about −210° C., which sets higher requirements for the material of the equipment. This greatly increases investment costs and results in high energy consumption.

CN201710006765.X discloses a process for separating reaction products produced by oxidative coupling of methane to ethylene. In the process, the reaction products are subjected to compression, an alcohol-amine method, drying, cryogenic rectification and other processes so as to separate the components one by one, and finally polymer grade ethylene product with an ethylene recovery rate of above 99% is obtained. The patent application significantly improves product quality, but a cryogenic rectification is still utilized in the separation, in which a cold box is required to provide a lower level of cooling capacity.

WO2015105911 discloses a system of oxidative coupling of methane, in which methane is converted to ethylene by oxidative coupling of methane, and then ethylene is converted to selectable higher hydrocarbon products. However, in this patent application, a low-temperature rectification is utilized to separate ethylene and the other components in the OCM product gas, such as unreacted methane, ethane, CO, $CO_2$, nitrogen, water, etc. The first separator is used to separate methane/nitrogen from components of C2 or higher, and the operating temperature of this separator is low to about −160° C. The second separator is used to separate methane and nitrogen, and its operating temperature is low to about −200° C.

SUMMARY OF THE INVENTION

The object of the present invention is to provide a method and a system for separating light hydrocarbons. The method can greatly increase the operating temperature of separating light hydrocarbon, has low energy consumption and a simple procedure, and is easy to operate and control. In addition, the method according to the present invention can greatly reduce the amount of the absorbent supplemented during operation by combining absorption and cracking.

In the first aspect, the present invention provides a method for separating light hydrocarbons, including the following steps:

(1) compressing and cooling C1-C4 hydrocarbon-containing hydrocarbon material to be separated to produce compressed and cooled hydrocarbon material, wherein the C1-C4 hydrocarbon-containing hydrocarbon material contains olefin(s) selected from C2 or more olefin and alkane(s) selected from C1-C4 alkane;

(2) contacting the compressed and cooled hydrocarbon material with an absorbent to absorb C2 or more hydrocarbons to produce a solvent-rich material;

(3) rectifying the solvent-rich material to produce a gas-phase material containing olefins and saturated alkanes and a solvent-lean material;

(4) rectifying the gas-phase material containing olefins and saturated alkanes one or more times to produce one or more streams of a saturated alkane-rich liquid-phase material;

(5) cracking the one or more streams of the saturated alkane-rich liquid-phase material to produce a cracked gas;

(6) circulating the cracked gas to the step (1).

In the second aspect, the present invention also provides a system for separating light hydrocarbons, which can be used to implement the method according to the first aspect of the present invention.

The system for separating light hydrocarbons provided by the present invention includes:

a compressing and cooling unit, an absorption unit, a desorption unit, a rectifying unit, and a cracking unit, wherein the absorption unit is connected to the compressing and cooling unit and the desorption unit respectively, the rectifying unit is connected to the desorption unit and the cracking unit respectively, and the cracking unit is connected to the compressing and cooling unit.

The present invention has the following beneficial effects:

1. The separation method provided by the present invention has a simple procedure and the obtained product has high product quality.

The present invention makes full use of the saturated resources, which greatly enhances the product value. In the present invention, the combination of cracking and absorption-desorption is used to separate light hydrocarbon materials such as OCM reaction gas. The saturated resources, such as ethane, propane, and butane, can be directly sent to a cracking furnace for treatment, and the cracked gas obtained and light hydrocarbons to be separated are sent to the separating device for treatment. The gas produced by cracking hydrocarbons such as ethane, propane, butane and so on contains abundant C2, C3 olefins as well as C4, C5 hydrocarbons. Therefore, on the one hand, the process according to the present application can improve yields of ethylene and propylene, on the other hand, the C4, C5 hydrocarbons in the cracked gas can be used as an absorbent in the absorption tower, reducing the amount of the absorbent supplemented in the system.

The separation method provided by the present invention can be implemented at a relatively high temperature, such as equal to or more than −35° C., or even equal to or more than 10° C. thereby reducing the requirements for the material of the equipment. A propylene refrigeration compressor can meet requirements of the cooling capacity in the entire process.

The process provided by the present invention is operated at a relatively high temperature, and the purification of the separated gas can be carried out after absorption-desorption. The main reason is as follows: after feeding the separated gas into the absorption tower, the gas mixture is separated by taking advantage of solubility difference between different components of the gas mixture in the solvent. The solubility of $CO_2$ and other impurities in the solvent is very low, and thus most of impurities such as $CO_2$ in the material can be removed through the absorption tower. This greatly reduces the processing capacity of the subsequent purifying unit(s) and reduces energy consumption. For light hydrocarbon materials with high $CO_2$ content, such as OCM reaction gas, the present invention can significantly reduce the energy consumption of the process.

BRIEF DESCRIPTION OF THE DRAWINGS

Exemplary embodiments of the present invention are described in more detail by referring to the accompanying drawings, and thus the above-mentioned and other objects, features, and advantages of the present invention will become more apparent. Among the exemplary embodiments of the present invention, the same reference numerals generally represent the same parts.

Figure 1:
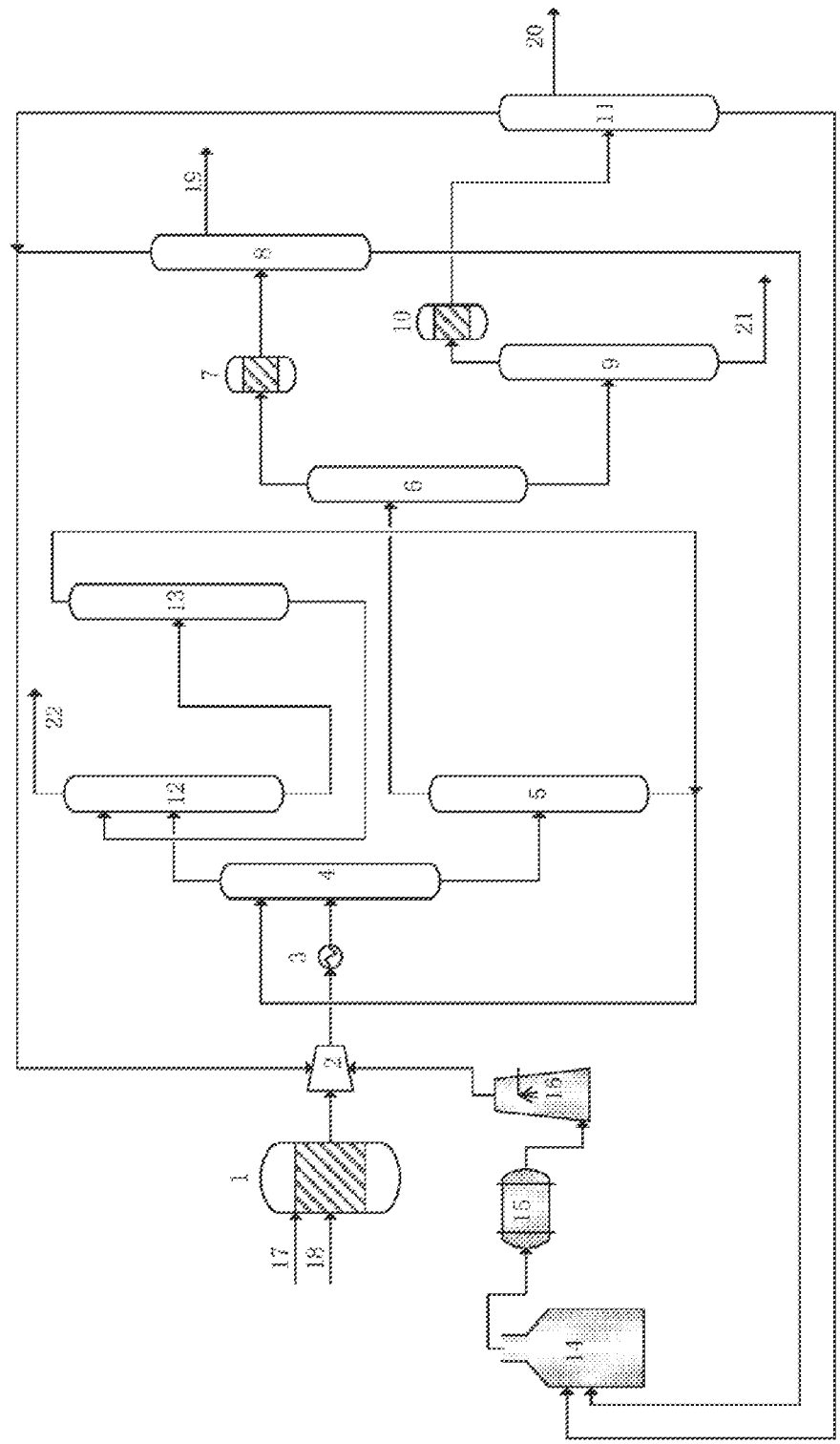
FIG. 1 shows a schematic flowchart of a method for separating the reaction gas from oxidative coupling of methane to ethylene according to Example 1 of the present invention.

Reference signs are described as follows.
1. reactor for oxidative coupling of methane to ethylene; 2. compressor; 3. heat exchanger; 4. first absorption tower (which may be referred to as absorption tower); 5. first rectifying tower (which may be referred to as desorption tower); 6. second rectifying tower (which may be referred to as deethanizer); 7. first hydrogenation reactor (which may be referred to as C2 hydrogenation reactor); 8. third rectifying tower (which may be referred to as ethylene rectifying tower); 9. fourth rectifying tower (which may be referred to as depropanizer); 10. second hydrogenation reactor (which may be referred to as C3 hydrogenation reactor); 11. fifth rectifying tower (which may be referred to as propylene rectifying tower); 12. second absorption tower (which may be referred to as re-absorption tower); 13. sixth rectifying tower (which may be referred to as gasoline desorption tower); 14. cracking furnace; 15. waste heat boiler; 16. oil washing tower/water washing tower; 17. oxygen or rich oxygen; 18. methane; 19. ethylene product; 20. propylene product; 21. C4 product; 22. exhaust gas; 23. cold box; 24. expander; 25. flash tank; 26. booster.

DETAILED DESCRIPTION OF THE EMBODIMENTS

Embodiments of the present invention will be described in detail below in conjunction with examples. It should be understood for those skilled in the art that, the following examples are only to illustrate the present invention and should not be considered to limit the scope of the present invention.

In the first aspect, the present invention provides a method for separating light hydrocarbons, including the following steps:

(1) compressing and cooling C1-C4 hydrocarbon-containing hydrocarbon material to be separated to produce compressed and cooled hydrocarbon material, wherein the C1-C4 hydrocarbon-containing hydrocarbon material contains olefin(s) selected from C2 or more olefin and alkane(s) selected from C1-C4 alkane;

(2) contacting the compressed and cooled hydrocarbon material with an absorbent to absorb C2 or more hydrocarbons to produce a solvent-rich material;

(3) rectifying the solvent-rich material to produce a gas-phase material containing olefins and saturated alkanes and a solvent-lean material;

(4) rectifying the gas-phase material containing olefins and saturated alkanes one or more times to produce one or more streams of a saturated alkane-rich liquid-phase material;

(5) cracking the one or more streams of the saturated alkane-rich liquid-phase material to produce a cracked gas;

(6) circulating the cracked gas to the step (1).

According to some embodiments of the present invention, in the step (6), the circulating the cracked gas to the step (1) includes: the cracked gas is combined with the C1-C4 hydrocarbon-containing hydrocarbon material to be separated and then they are compressed and cooled together; or the cracked gas is compressed and then combined with the compressed C1-C4 hydrocarbon-containing hydrocarbon material, and they are cooled; or the cracked gas is compressed and cooled, and then combined with the compressed and cooled C1-C4 hydrocarbon-containing hydrocarbon material.

According to some embodiments of the present invention, the C1-C4 hydrocarbon-containing hydrocarbon material is one or more selected from reaction gas of oxidation of methane to ethylene, refinery dry gas, dry gas of chemical processing of coal, catalytically cracked products, Fischer-Tropsch exhaust gas, propane dehydrogenated product, flare gas/separated methane gas (also called Gas), and separated shale gas. In some embodiments, the C1-C4 hydrocarbon-containing hydrocarbon material is obtainable from the reaction gas of oxidation of methane to ethylene (abbreviated as "OCM reaction gas").

According to some embodiments of the present invention, the C2 or more olefin is selected from one or more of ethylene, propylene, 1-butene, 2-butene, and 1,3-butadiene.

According to some embodiments of the present invention, the C1-C4 alkane is selected from one or more of methane, ethane, propane, n-butane, and iso-butane.

According to some embodiments of the present invention, the saturated alkane is selected from one or more of ethane, propane, n-butane and iso-butane. According to some examples, the one or more streams of the saturated alkane-rich liquid-phase material include ethane-rich liquid-phase material. The one or more streams of the saturated alkane-rich liquid-phase material include ethane-rich liquid-phase material and propane-rich liquid-phase material.

According to some embodiments of the present invention, in the step (4), while one or more streams of the alkane-rich liquid-phase material are obtained, one or more streams of olefin-rich liquid-phase or gas-phase material are obtained. According to some examples, the one or more streams of olefin-rich liquid-phase material include ethylene-rich liquid-phase or gas-phase material. The one or more streams of olefin-rich liquid-phase material include include ethylene-rich gas-phase or liquid-phase materials and propylene-rich gas-phase or liquid-phase material.

In the present invention, the term "rich" means that the molar content of a component in the material accounts for equal to or more than 50%, such as equal to or more than 80%, equal to or more than 90%, equal to or more than 95%, equal to or more than 98%, or equal to or more than 99%.

According to some embodiments of the present invention, the absorbent is a C3 fraction containing C3 alkane, a C4 fraction containing C4 alkane, and a C5 fraction containing C5 alkane.

According to some embodiments of the present invention, the C3 alkane is n-propane, the C4 alkane is n-butane, and the C5 alkane is selected from n-pentane and iso-pentane.

According to some embodiments of the present invention, the temperature of the cracking is 500-850° C. and preferably 600-800° C. The cracked gas contains olefins and alkanes.

In this application, "saturated alkane" and "alkane" are interchangeable. According to some embodiments of the present invention, in the step (1), the C1-C4 hydrocarbon-containing hydrocarbon material is compressed to 2.0-5.0 MPa.

According to some embodiments of the present invention, the C1-C4 hydrocarbon-containing hydrocarbon material is cooled to −40° C. to 20° C., such as, 5° C. to 20° C. or −40° C. to −10° C.

According to some embodiments of the present invention, in the step (2), the compressed and cooled hydrocarbon material is contacted with the absorbent in the first absorption tower, obtaining a gas-phase stream containing light components from the top of the tower and a solvent-rich material from the kettle. Preferably, the theoretical plate number of the first absorption tower is 30-80, and the operating pressure is 2.0-6.0 MPa.

According to some embodiments of the present invention, in the step (3), an absorption liquid is fed into a first rectifying tower for rectification, obtaining a gas-phase material containing olefins and saturated alkanes from the top of the tower and a solvent-lean material from the kettle. The purpose of the step (3) is to desorb the absorption liquid.

According to some embodiments of the present invention, the method further includes purifying the gas-phase material containing olefins and saturated alkanes obtained from the top of the first rectifying tower after the step (3), so as to remove acidic components and/or moisture therein. The purified material is then subjected to the step (4).

According to some embodiments of the present invention, the method further includes purifying the compressed hydrocarbon material in the step (1), so as to remove acidic components and/or moisture therein. The purified material is then cooled.

According to some embodiments of the present invention, the theoretical plate number of the first rectifying tower is 20-60, and the operating pressure is 1.0-4.0 MPa.

According to some embodiments of the present invention, the step (4) includes:

feeding the gas-phase material containing olefins and saturated alkanes into a second rectifying tower for rectification, obtaining a first stream containing ethane and ethylene from the top of the tower and a second stream containing C3 more hydrocarbons from the kettle; feeding the first stream into a third rectifying tower for rectification, obtaining an ethylene product stream on the side, a third stream containing ethylene from the top of the tower, and an ethane-rich fourth stream from the kettle.

Optionally, the first stream is fed into a first hydrogenation reactor for selective hydrogenation before being fed into the third rectifying tower, so as to remove alkyne and/or alkadiene.

According to some embodiments of the present invention, the theoretical plate number of the second rectifying tower is 30-80, and the operating pressure is 1.0-5.0 MPa.

According to some embodiments of the present invention, the theoretical plate number of the third rectifying tower is 50-130, and the operating pressure is 1.0-4.0 MPa.

According to some embodiments of the present invention, the step (4) further includes:

the second stream is rectified in a fourth rectifying tower, obtaining a fifth stream containing propane and propylene from the top of the tower and a saturated alkane-rich sixth stream from the kettle.

According to some embodiments of the present invention, the theoretical plate number of the fourth rectifying tower is 30-80, and the operating pressure is 0.1-3.0 MPa.

According to some embodiments of the present invention, the step (4) further includes:

feeding the fifth stream into a fifth rectifying tower for rectification, obtaining a stream of propylene product on the side, a seventh stream containing propylene from the top of the tower, and a propane-rich eighth stream from the kettle.

Optionally, the fifth stream is fed into a second hydrogenation reactor for selective hydrogenation before being fed into the fifth rectifying tower, so as to remove alkyne and/or alkadiene.

Optionally, part or all of the seventh stream is circulated to the step (1).

Preferably, the theoretical plate number of the fifth rectifying tower is 100-200, and the operating pressure is 1.0-4.0 MPa.

According to some embodiments of the present invention, one or more of the fourth stream, the sixth stream and the eighth stream, preferably all are cracked to produce cracked gas. The resulting cracked gas contains olefins and alkanes. Part or all of the cracked gas is circulated to the step (1), which not only increases the yield of olefins, but also decreases the amount of the supplemented absorbent.

According to some embodiments of the present invention, the step (4) further includes the following steps:

The second stream is rectified in the fifth rectifying tower, obtaining a stream of propylene product on the side, a ninth stream containing propylene from the top of the tower, and a saturated alkane-rich tenth stream from the kettle.

Optionally, part or all of the ninth stream is circulated to the step (1).

Optionally, the second stream is fed into a third hydrogenation reactor for selective hydrogenation before being fed into the fifth rectifying tower, so as to remove alkyne and/or alkadiene.

Preferably, the theoretical plate number of the fifth rectifying tower is 100-200, and the operating pressure is 1.0-4.0 MPa.

According to some embodiments of the present invention, one or all of the fourth stream and the sixth stream are cracked to produce cracked gas. The resulting cracked gas contains olefins and alkanes. Part or all of the cracked gas is circulated to the step (1), which not only increases the yield of olefins, but also decreases the amount of the supplemented absorbent.

According to some embodiments of the present invention, the solvent-lean material is fed into the first absorption tower as a circulating absorbent.

According to some embodiments of the present invention, the gas-phase stream containing light components from the top of the first absorption tower is fed into the second absorption tower to contact with a re-absorbent therein to absorb the entrained absorbent and C2 hydrocarbon that is not absorbed by the absorbent in the first absorption tower. Preferably, the re-absorbent is selected from gasoline, heavy naphtha, and aromatic residual oil.

Preferably, the theoretical plate number of the second absorption tower is 15-60, and the operating pressure is 1.0-5.0 MPa.

According to some embodiments of the present invention, the exhaust gas obtained from the top of the second absorption tower is discharged outside the boundary area, and the liquid-phase material obtained from the kettle is discharged outside the boundary area or subjected to other treatments.

According to some embodiments of the present invention, the other treatments include: the liquid-phase material obtained from the second absorption tower is fed into the sixth rectifying tower for rectification, and the gas-phase stream obtained from the top of the sixth rectifying tower is fed into the first absorption tower as a circulating absorbent, the liquid-phase stream obtained from the kettle is fed into the second absorption tower as a circulating re-absorbent.

Preferably, the theoretical plate number of the sixth rectifying tower is 10-50, and the operating pressure is 0.1-2.0 MPa.

According to some embodiments of the present invention, the gas-phase stream containing light components from the top of the first absorption tower is subjected to cold energy recovery, preferably the cold energy recovery is performed in a cold energy recovery unit, preferably, the cold energy recovery unit includes a cold box, an expander, a booster and a flash tank.

According to some embodiments of the present invention, the gas-phase stream containing light components is cooled through the cold box, and then expanded and flashed to recover unabsorbed C2 hydrocarbons and the entrained absorbent, the exhaust gas without C2 hydrocarbons is pressurized by a booster driven by an expander and then discharged.

According to some embodiments of the present invention, the gas-phase stream containing light components is fed into the cold box to be cooled to −80° C. to −35° C., expanded by an expander, and then fed into a flash tank for flash evaporation. The gas from the top of the flash tank is fed into the cold box, and then is boosted by a booster driven by the expander and discharged, while the liquid from the bottom of the flash tank is sent back to the top of the first absorption tower.

According to some embodiments of the present invention, the cracked gas is fed into a waste heat boiler to recover heat, fed into an oil washing tower and/or a water washing tower, and then is circulated to the step (1) for compression.

A system for separating light hydrocarbons provided by the present invention includes:

a compressing and cooling unit, an absorption unit, a desorption unit, a rectifying unit, and a cracking unit, wherein the absorption unit is connected to the compressing and cooling unit and the desorption unit respectively, the rectifying unit is connected to the desorption unit and the cracking unit respectively, and the cracking unit is connected to the compressing and cooling unit.

According to some embodiments of the present invention, the compressing and cooling unit includes a compressor 2 and a heat exchanger 3, the absorption unit includes a first absorption tower 4, the desorption unit includes a first rectifying tower 5, the rectifying unit includes a second rectifying tower 6 and a third rectifying tower 8, and the cracking unit includes a cracking furnace 14.

The type of cracking furnace used in the present invention is not particularly limited. The cracked gas is fed into a waste heat boiler to recover heat, and then is cooled through a water washing tower. If necessary, an oil washing tower can also be provided in the cracking step.

According to some embodiments of the present invention, the outlet of the compressor 2 is connected to the inlet of the heat exchanger 3, and the outlet of the heat exchanger 3 is connected to the first inlet of the first absorption tower 4, the kettle outlet of the first absorption tower 4 is connected to the inlet of the first rectifying tower 5, and the top outlet of the first rectifying tower 5 is connected to the inlet of the second rectifying tower 6.

According to some embodiments of the present invention, the top outlet of the second rectifying tower 6 is connected to the inlet of the third rectifying tower 8, and the kettle outlet of the third rectifying tower 8 is connected to the first inlet of the cracking furnace 14. Optionally, a first hydrogenation reactor 7 is arranged between the top of the second rectifying tower 6 and the third rectifying tower 8. Optionally, the top outlet of the third rectifying tower 8 is connected to the inlet of the compressor 2.

According to some embodiments of the present invention, the rectifying unit further includes a fourth rectifying tower 9, wherein the inlet of the fourth rectifying tower 9 is connected to the kettle outlet of the second rectifying tower 6, and the kettle outlet of the fourth rectifying tower 9 is connected to the first inlet and/or the second inlet of the cracking furnace 14.

According to some embodiments of the present invention, the rectifying unit further includes a fifth rectifying tower 11, wherein the top outlet of the fourth rectifying tower 9 is connected to the inlet of the fifth rectifying tower 11. A second hydrogenation reactor 10 is optionally arranged between the fifth rectifying tower 11 and the fourth rectifying tower 9, the kettle outlet of the fifth rectifying tower is connected to the first inlet and/or the second inlet and/or the third inlet of the cracking furnace, and optionally, the top outlet of the fifth rectifying tower 11 is connected to the first inlet of the compressor 2.

According to some embodiments of the present invention, the cracking unit further includes a waste heat boiler 15 and an oil washing tower and/or water washing tower 16, wherein the outlet of the cracking furnace 14 is connected to the inlet of the waste heat boiler 15, the outlet of the waste heat boiler 15 is connected to the inlet of the oil washing tower and/or water washing tower 16, and the outlet of the oil washing tower and/or water washing tower 16 is connected to the first inlet and/or the second inlet of the compressor 2.

According to some embodiments of the present invention, the kettle outlet of the first absorption tower 4 is connected to the inlet of the first rectifying tower 5, the top outlet of the first absorption tower 4 is connected to the first inlet of a second absorption tower 12, and the kettle outlet of the second absorption tower 12 is optionally connected to the inlet of a sixth rectifying tower 13.

According to some embodiments of the present invention, the top outlet of the sixth rectifying tower 13 is connected to the second inlet of the first absorption tower 4, and the kettle outlet of the sixth rectifying tower 13 is connected to the second inlet of the second absorption tower 12.

According to some embodiments of the present invention, the kettle outlet of the first absorption tower 4 is connected to the inlet of the first rectifying tower 5, and the top outlet of the first absorption tower 4 is connected to the cold energy recovery unit.

According to some embodiments of the present invention, the cold energy recovery unit includes a cold box 23, an expander 24, a flash tank 25 and a booster 26, wherein the first inlet of the cold box is connected to the top outlet of the first absorption tower 4, the first outlet of the cold box is connected to the inlet of the expander, the outlet of the expander is connected to the inlet of the flash tank, the first outlet of the flash tank is connected to the second inlet of the cold box, the second outlet of the cold box is connected to the inlet of the booster, and optionally the second outlet of the flash tank is connected to the second inlet of the first absorption tower.

According to some embodiments of the present invention, the system further includes a purification device arranged between the first rectifying tower and the second rectifying tower, for removing acid gas and/or moisture from the material obtained from the top of the first rectifying tower.

According to other embodiments of the present invention, the system further includes a purification device arranged between the compressor and the heat exchanger, for removing acid gas and/or moisture from the material obtained from the compressor.

The inlets of the rectifying towers including the first rectifying tower, the second rectifying tower, the third rectifying tower, the fourth rectifying tower, the fifth rectifying tower, and the sixth rectifying tower are usually arranged on the side wall of the tower body, and preferably in the middle of the side wall.

The inlets of the first absorption tower and the second absorption tower are usually arranged on the side wall of the tower body, and preferably on the upper part of the side wall.

Example 1

The reaction gas of oxidative coupling of methane to ethylene is separated by using the separating method as shown in FIG. 1.

The procedure of the process is as follows.

Methane 18 and oxygen or rich oxygen 17 are reacted in a reactor for oxidative coupling of methane to ethylene 1 to obtain OCM reaction gas. The resulting OCM reaction gas is gradually pressurized by a compressor 2, cooled by a heat exchanger 3, and then fed into an absorption tower 4. The gas from the top of the absorption tower 4 is fed into a re-absorption tower 12, and the material from the bottom of the absorption tower 4 is fed into a desorption tower 5. The exhaust gas 22 from the top of the re-absorption tower 12 is sent to the outside of the boundary area, and the stream from the kettle is fed into the gasoline desorption tower 13. The lean solvent from the kettle of the desorption tower 5 is heat exchanged and then sent back to the absorption tower 4, and the gas phase extracted from the top of the desorption tower 5 is fed into the deethanizer 6. The material from the top of the deethanizer 6 is fed into C2 hydrogenation reactor 7 to remove alkyne and then fed into ethylene rectifying tower 8. The gas phase from the top of the ethylene rectifying tower 8 is sent back to the middle section of the compressor, ethylene product 19 is obtained on the side, and the material from the kettle is sent to the cracking furnace 14. The material from the kettle of the deethanizer 6 is sent to depropanizer 9. The material from the top of the depropanizer 9 is fed into C3 hydrogenation reactor 10 to remove alkyne and then fed into propylene rectifying tower 11. The gas phase from the top of the propylene rectifying tower 11 is sent back to the middle section of the compressor, propylene product 20 is obtained on the side, and the material from the kettle is sent to the cracking furnace 14. The material from the kettle of the depropanizer 9 is obtained as C4 product 21. The cracked gas obtained by the cracking in the cracking furnace 14 is subjected to heat recovery in the waste heat boiler 15, fed into the oil washing tower/water washing tower 16, and then fed into the first suction tank of the compressor 2.

The composition of reaction gas in the outlet of the reactor for oxidative coupling of methane to ethylene is shown in Table 1.

TABLE 1

| Composition | mol % |
|---|---|
| Oxygen | 0.55 |
| CO | 5.69 |
| $CO_2$ | 6.15 |
| Methane | 34.06 |
| Ethylene | 7.72 |
| Ethane | 2.52 |
| Propane | 0.55 |
| Water | 42.75 |
| Alkyne | 0.01 |

The specific steps are as follows.

(1) Compression: OCM reaction gas is sent to a compressing system and subjected to five stages of compression, the pressure of which increased to 4.2 MPa.

(2) Cooling: the pressurized OCM reaction gas is cooled to 15° C. and then fed into the absorption tower 4.

(3) Absorption: the theoretical plate number of the absorption tower 4 is 55 and the operating pressure is 3.8 MPa. The used absorption solvent is etherified C4. The absorption solvent is fed into the tower from the top of the absorption tower, and the OCM reaction gas is fed in the 30th tray. C2 and above components in the OCM reaction gas are absorbed by the solvent and are extracted from the kettle.

Light components such as methane, oxygen, and CO with a small amount of the absorbent are extracted from the top of the tower.

(4) Desorption: the theoretical plate number of the desorption tower 5 is 40, the operating pressure is 2.4 MPa, and the operating temperature is about 15° C. After desorption, the gas phase from the top of the tower is sent to the purification unit, and the lean solvent from the kettle is heat exchanged stepwise and cooled to 15° C., and then sent back to the absorption tower 4 for recycling.

(5) Purification: after deacidification in an amine washing/alkali washing tower, the deacidified gas is dried.

(6) Deethanization: the purified material is fed into the deethanizer. The theoretical plate number of the deethanizer is 50, the operating pressure is 2.0 MPa, and the operating temperature is −20° C. The material rich in ethylene and ethane is extracted from the top of the deethanizer 6 and sent to C2 hydrogenation reactor to remove alkyne such as acetylene taking advantage of hydrogenation, and the material from the kettle of the deethanizer is sent to the depropanizer.

(7) Ethylene rectification: the material from the C2 hydrogenation reactor is fed into the ethylene rectifying tower 8, the theoretical plate number of the ethylene rectifying tower is 90, the operating pressure is 2.0 MPa. and the operating temperature is −35° C. The gas phase from the top of the ethylene rectifying tower is sent back to the four-stage inlet of the compressor, and ethylene product is obtained on the side, and the material from the kettle is sent to the cracking furnace 14.

(8) Depropanization: the theoretical plate number of the depropanizer 9 is 40, the operating pressure is 0.7 MPa, and the operating temperature of the depropanizer is 16° C. The material from the top of the depropanizer is sent to the C3 hydrogenation reactor to remove alkyne and alkadiene, and the material from the kettle of the depropanizer is obtained as C4 product.

(9) Propylene rectification: the material from the C3 hydrogenation reactor is fed into the propylene rectifying tower. The theoretical plate number of the propylene rectifying tower is 160, the operating pressure is 1.7 MPa, and the operating temperature is 40° C. The gas phase from the top of the propylene rectifying tower is sent back to the four-stage inlet of the compressor, propylene product is obtained on the side, and the main material from the kettle is propane, which is sent to the cracking furnace.

(10) Cracking: the materials from the kettle in steps (7) and (9) are fed into the cracking furnace, alkanes such as ethane, propane, n-butane in the materials are cracked. The outlet temperature of the cracking furnace is equal to or below 850° C., and the residence time of the materials in the cracking furnace is equal to or less than 0.3 seconds. The cracked gas is subjected to heat recovery in the waste heat boiler, cooled in the water washing tower, and then fed into the first stage inlet of the compressor.

(11) Re-absorption: the gas from the top of the absorption tower is fed into the re-absorption tower. The theoretical plate number of the re-absorption tower is 20 and the operating pressure is 3.8 MPa. The re-absorbent is added from the top of the tower to absorb the entrained absorbent and unabsorbed C2 component. The exhaust gas from the top of the re-absorption tower is sent outside the boundary area, and the stream from the kettle is sent to the gasoline desorption tower.

(12) Gasoline desorption: the stream from the kettle of the re-absorption tower is fed into the gasoline desorption tower. The theoretical plate number of the gasoline desorption tower is preferably 28, the operating pressure is 0.5 MPa, and the operating temperature is 15° C. The gas from the top of the gasoline desorption tower is cooled and then sent to the absorption tower. The gasoline-lean solvent obtained from the kettle is cooled and sent back to the re-absorption tower.

The composition of the resulting ethylene product is shown in Table 2, and the yield of the ethylene product is shown in Table 12. The composition of the resulting propylene product is shown in Table 3.

TABLE 2

| Composition | mol % |
| --- | --- |
| methane | 0.05 |
| ethylene | 99.95 |

TABLE 3

| Composition | mol % |
| --- | --- |
| propylene | 95.2 |
| propane | 4.8 |

In this example, the purity of the ethylene product meets the specifications of polymer grade ethylene, the purity of the propylene product meets the specifications of chemical grade propylene, and the ethylene recovery rate is 99.7%.

For this example, due to the arrangement of a cracking furnace and that additional cracked gas is included in the gas entering the absorption tower, so that the amount of the supplemented absorbent can be reduced by about 22%, referring to Table 6 for details.

Example 2

Figure 2:
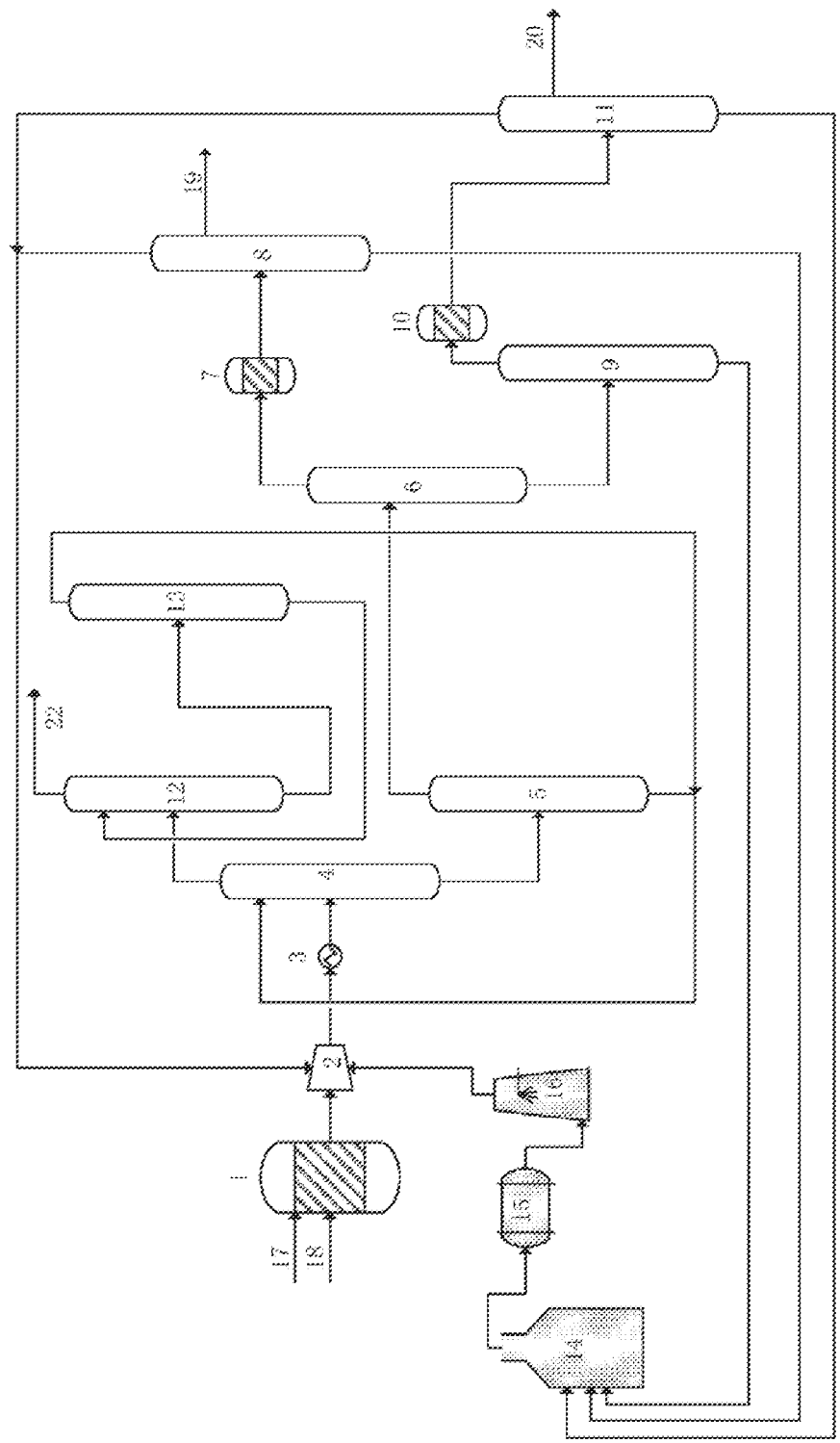
FIG. 2 shows a schematic flowchart of a method for separating the reaction gas from oxidative coupling of methane to ethylene according to Example 2 of the present invention.

The reaction gas of oxidative coupling of methane to ethylene is separated by using the separating method as shown in FIG. 2.

The procedure of the process is as follows. Methane 18 and oxygen or rich oxygen 17 are reacted in a reactor for oxidative coupling of methane to ethylene 1 to obtain OCM reaction gas. The resulting OCM reaction gas is gradually pressurized by a compressor 2, cooled by a heat exchanger 3, and then fed into an absorption tower 4. The gas from the top of the absorption tower 4 is fed into a re-absorption tower 12, and the material from the bottom of the absorption tower 4 is fed into a desorption tower 5. The exhaust gas 22 from the top of the re-absorption tower 12 is sent to the outside of the boundary area, and the stream from the kettle is fed into the gasoline desorption tower 13. The lean solvent from the kettle of the desorption tower 5 is heat exchanged and then sent back to the absorption tower 4, and the gas phase extracted from the top of the desorption tower 5 is fed into the deethanizer 6. The material from the top of the deethanizer 6 is fed into C2 hydrogenation reactor 7 to remove alkyne and then fed into the ethylene rectifying tower 8. The gas phase from the top of the ethylene rectifying tower 8 is sent back to the intersegment of the compressor, ethylene product 19 is obtained on the side, and the material from the kettle is sent to the cracking furnace 14. The material from the kettle of the deethanizer 6 is sent to depropanizer 9. The material from the top of the depropanizer 9 is fed into C3 hydrogenation reactor 10 to remove alkyne and then fed into propylene rectifying tower 11. The gas phase from the top of the propylene rectifying tower 11 is sent back to the intersegment of the compressor, propylene product 20 is obtained on the side, and the material from the kettle is sent to the cracking furnace 14. The material from the kettle of the depropanizer 9 is fed into the cracking furnace 14. The cracked gas obtained by the cracking in the cracking furnace 14 is subjected to heat recovery in the waste heat boiler 15, fed into the oil washing tower/water washing tower 16, and then fed into the first suction tank of the compressor 2.

The specific steps are as follows: the differences between this example and the Example 1 only are that n-butane is selected as the absorbent; and the material from the kettle of the depropanizer 9 is also sent to the cracking furnace 14.

The composition of reaction gas in the outlet of the reactor for oxidative coupling of methane to ethylene is shown in Table 1.

The composition of the resulting ethylene product is shown in Table 4, and the yield of the ethylene product is shown in Table 12.

TABLE 4

| Composition | mol % |
|---|---|
| methane | 0.05 |
| ethylene | 99.95 |

The composition of the resulting propylene product is shown in Table 5.

TABLE 5

| Composition | mol % |
|---|---|
| propylene | 95.2 |
| propane | 4.8 |

In this example, the purity of the ethylene product meets the specifications of polymer grade ethylene, the purity of the propylene product meets the specifications of chemical grade propylene, and the ethylene recovery rate is 99.5%.

For this example due to the arrangement of a cracking furnace and that additional cracked gas is included in the gas entering the absorption tower, so that the amount of the supplemented absorbent can be reduced by about 30%, referring to Table 6 for details.

Comparative Example 1

The differences from Example 2 only are that a cracking furnace is not arranged, and the materials from the kettle in steps (7), (8) and (9) are discharged beside the boundary area.

TABLE 6

| | The amount of supplemented absorbent kg/h |
|---|---|
| Example 1 | 5944.96 |
| Example 2 | 5464.43 |
| Comparative Example 1 | 7146.27 |
| Reduction of the supplemented absorbent of Example 1 relative to that of Comparative Example 1 | 1201.31 |
| Reduction percent of the supplemented absorbent of Example 1 relative to that of Comparative Example 1 | 22% |

TABLE 6-continued

| | The amount of supplemented absorbent kg/h |
|---|---|
| Reduction of the supplemented absorbent of Example 2 relative to that of Comparative Example 1 | 1681.84 |
| Reduction percent of the supplemented absorbent of Example 2 relative to that of Comparative Example 1 | 30.80% |

It can be seen from the comparison of Examples 1 and 2 with Comparative Example 1 that, due to that the materials comprising those from the kettle of the ethylene rectifying tower, the propylene rectifying tower and/or depropanizer are fed into the cracking furnace to crack, and then circulated to the compression section, under the same ethylene recovery rate, the same heavy component recovery, and similar solvent ratio, the amount of the supplemented absorbent significantly decreased.

Meanwhile, because part of $CO_2$ can be processed in the absorption tower, the volume of $CO_2$ needed to be subsequently decarbonized can be significantly reduced. The specific results are shown in Table 7 below.

TABLE 7

| | Example 1 | Example 2 |
|---|---|---|
| Amount of $CO_2$ into the absorption tower kg/h | 16771 | 16725 |
| Amount of $CO_2$ from the top of the absorption tower kg/h | 3081 | 6958 |
| Reduction of $CO_2$/% | 18.4 | 41.6 |

Example 3

Figure 3:
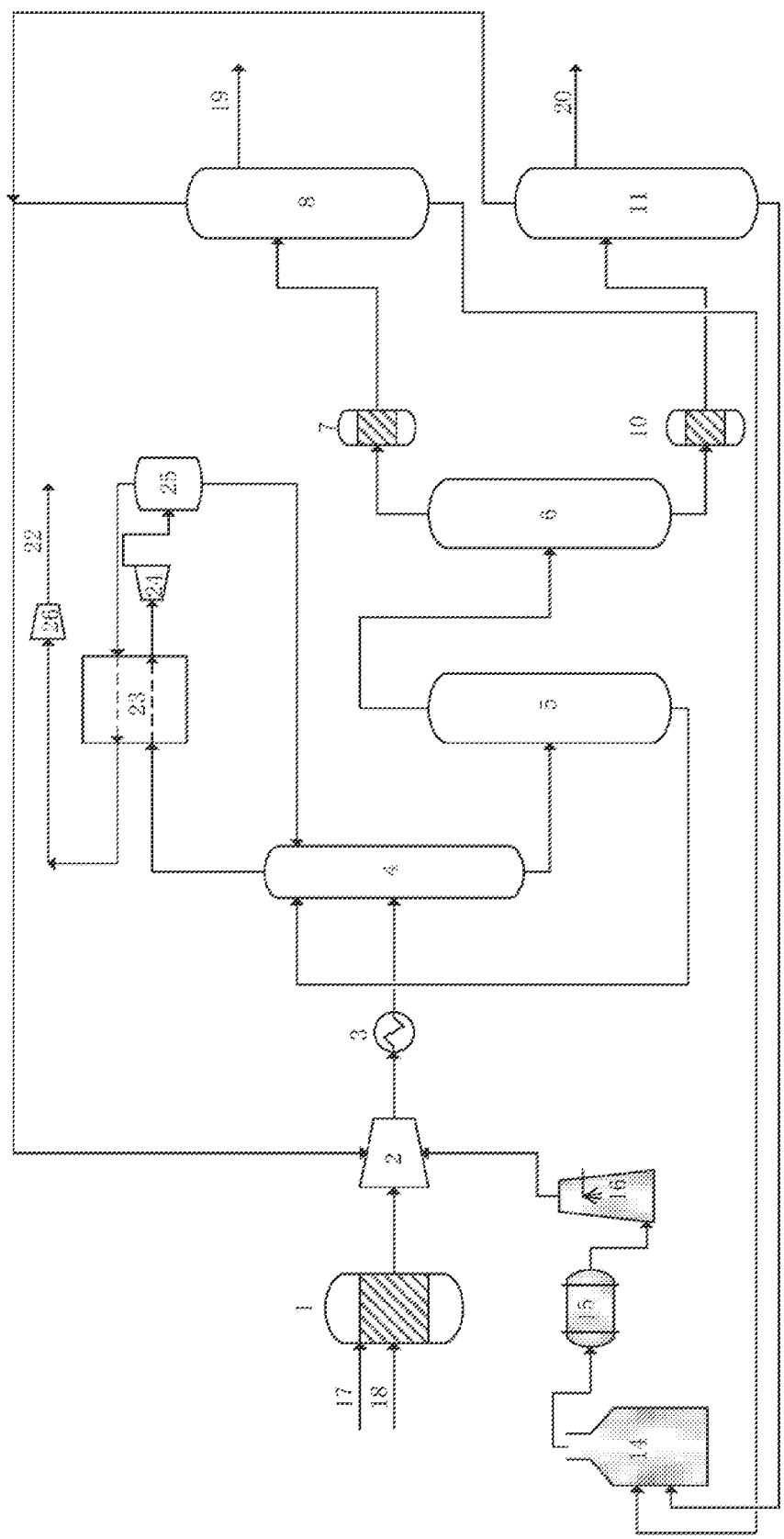
FIG. 3 shows a schematic flowchart of a method for separating the reaction gas from oxidative coupling of methane to ethylene according to Example 3 of the present invention.

The reaction gas of oxidative coupling of methane to ethylene is separated by using the separating method as shown in FIG. 3.

The procedure of the process is as follows.

Oxygen or rich oxygen 17 and methane 18 are fed into a reactor for oxidative coupling of methane to ethylene 1 and subjected to oxidative coupling reaction. The resulting OCM reaction gas is gradually pressurized by the compressor 2, cooled by the heat exchanger 3, and then fed into an absorption tower 4. The gas from the top of the absorption tower 4 is cooled by the cold box 23, is fed into the expander 24 to expand the gas, and then fed into a flash tank 25 for flash evaporation. The exhaust gas 22 from the top of the flash tank 25 is fed into the cold box 23, pressurized in a booster 26 driven by the expander 24 and then discharged, and the liquid from the bottom of the flash tank 25 is sent back to the top of the absorption tower 4. The material from the bottom of the absorption tower 4 is fed into the desorption tower 5. The lean solvent from the kettle of the desorption tower 5 is heat exchanged and then sent back to the top of the absorption tower 4, and the gas extracted from the top of the desorption tower 5 is fed into the deethanizer 6. The material from the top of the deethanizer 6 is fed into C2 hydrogenation reactor 7 and then fed into ethylene rectifying tower 8, and the material from the kettle of the deethanizer 6 is fed into C3 hydrogenation reactor 10 and then fed into propylene rectifying tower 11. Ethylene product 19 is obtained on the side of the ethylene rectifying tower 8, the gas from the top is sent back to the intersegment of the compressor 2, and the ethane from the kettle is sent to the cracking furnace 14. Propylene product 20 is obtained on the side of the propylene rectifying tower 11, the gas phase from the top is sent back to the intersegment of the compressor 2, and propane from the kettle is sent to the cracking furnace 14. The cracked gas obtained by the cracking in the cracking furnace 14 is subjected to heat recovery in the waste heat boiler 15, fed into the oil washing tower/water washing tower 16, and then fed into the first suction tank of the compressor 2.

The composition of reaction gas in the outlet of the reactor for oxidative coupling of methane to ethylene is shown in Table 1.

Specifically, the method comprises the following steps.

(1) Compression: OCM reaction gas is sent to the compression system for three stages of compression, the pressure of which is increased to 1.0 MPa, and then sent to the amine washing tower for purification.

(2) Purification: the OCM reaction gas is subjected to deacidification in the amine washing tower and then is dried.

(3) Cooling: the purified gas continues to be compressed, the pressure of which is increased to 3 MPa, cooled to −35° C. stepwise, and then is fed into the absorption tower.

(4) Absorption: the theoretical plate number of the absorption tower is 55, the operating pressure is 2.7 MPa, and the tower top temperature is −27° C. The absorption solvent used is a propane-rich C3 fraction, the solvent is fed into the tower from the top of the absorption tower, and the OCM reaction gas is fed in the 30th tray. C2 and above components in the OCM reaction gas are absorbed by the solvent and are extracted from the kettle. Light components such as methane, oxygen, and CO with a small amount of the absorbent are extracted from the top of the tower.

(5) Desorption: the theoretical plate number of the desorption towers is 30, and the operating pressure is 2.2 MPa. After desorption, the gas from the top of the desorption tower is sent to the deethanizer, and the lean solvent from the kettle is heat exchanged stepwise and cooled to −35° C. and then sent back to the absorption tower for recycling.

(6) Deethanization: the theoretical plate number of the deethanizer is 50, and the operating pressure is 2.0 MPa. C2 component rich in ethylene and ethane is extracted from the top of the deethanizer, and C3 component rich in propylene and propane is extracted from the kettle of the deethanizer.

(7) Ethylene rectification: the theoretical plate number of the ethylene rectifying tower is 90, and the operating pressure is 2.0 MPa. The gas from the top of the deethanizer is sent to the C2 hydrogenation reactor to remove the alkyne and then sent to the ethylene rectifying tower. The gas from the top of the ethylene rectifying tower is sent back to the four-stage inlet of the compressor, the ethylene product is obtained on the side, and the ethane-rich product is obtained from the kettle and sent to the cracking furnace.

(8) Propylene rectification: The theoretical plate number of the propylene rectifying tower is 140, and the operating pressure is 1.7 MPa. The material from the kettle of the deethanizer is sent to the C3 hydrogenation reactor to remove alkyne, alkadiene, and then sent to the propylene rectifying tower. Propylene product is obtained on the side of the propylene rectifying tower, the gas from the top is sent back to the four-stage inlet of the compressor, and the propane-rich product is obtained from the kettle and sent to the cracking furnace.

(9) Cracking: the ethane-rich product obtained in step (7) and the propane-rich product obtained in step (8) are fed into the cracking furnace. The cracking temperature is equal to or below 850° C., and the residence time is equal to or below 0.3 seconds. The resulting cracked gas is subjected to heat recovery in the waste heat boiler, cooled in the oil washing tower/water washing tower, and then fed into the first suction tank of the compressor.

(10) Cold energy recovery: the unabsorbed gas from the top of the absorption tower is fed into the cold box to reduce the temperature to −45° C., and then fed into the flash tank for flash evaporation. The liquid from the bottom of the flash tank is sent back to the top of the absorption tower, and the exhaust gas rich in components such as methane, oxygen, CO is fed into the cold box, pressurized in a booster driven by the expander and then discharged.

The composition of the resulting ethylene product is shown in Table 8, and the yield of the ethylene product is shown in Table 12.

TABLE 8

| Composition | mol % |
| --- | --- |
| methane | 0.03 |
| ethylene | 99.95 |
| ethane | 0.02 |

The composition of the resulting propylene product is shown in Table 9.

TABLE 9

| Composition | mol % |
| --- | --- |
| propylene | 95.2 |
| propane | 4.8 |

Example 4

Figure 4:
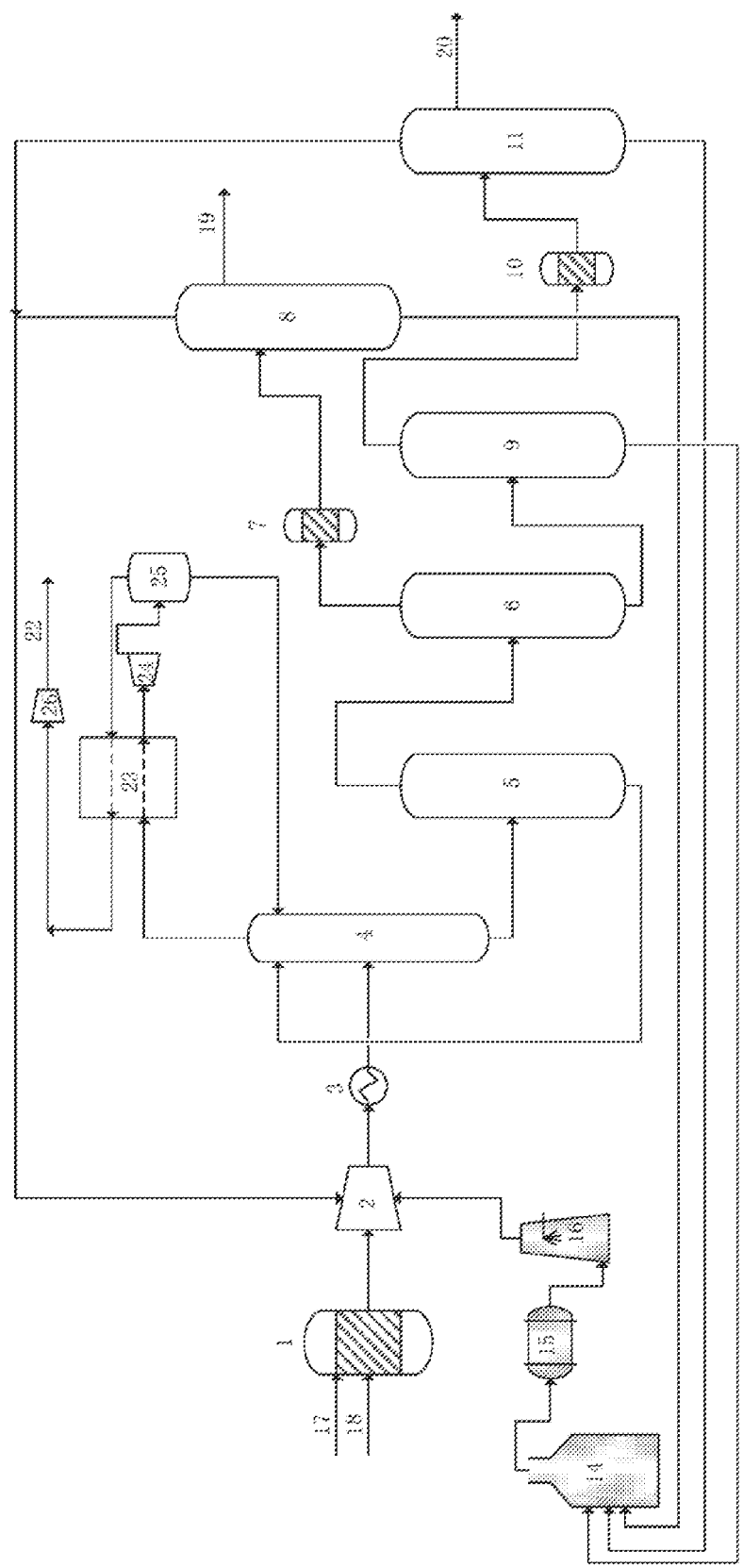
FIG. 4 shows a schematic flowchart of a method for separating the reaction gas from oxidative coupling of methane to ethylene according to Example 4 of the present invention.

The reaction gas of oxidative coupling of methane to ethylene is separated by using the separating method as shown in FIG. 4.

The composition of reaction gas in the outlet of the reactor for oxidative coupling of methane to ethylene is shown in Table 1.

Specifically, the method comprises the following steps.

(1) Compression: OCM reaction gas is sent to the compression system for three stages of compression, the pressure of which is increased to 1.0 MPa, and then sent to the amine washing tower for purification.

(2) Purification: the OCM reaction gas is subjected to deacidification in the amine washing tower and then is dried.

(3) Cooling: The purified gas continues to be compressed, the pressure of which is increased to 3 MPa, cooled to −35° C. stepwise, and then is fed into the absorption tower.

(4) Absorption: the theoretical plate number of the absorption tower is 55, the operating pressure is 2.7 MPa. and the tower top temperature is −27° C. The absorption solvent used is n-butane, the solvent is fed into the tower from the top of the absorption tower, and the OCM reaction gas is fed in the 30th tray. C2 and above components in the OCM reaction gas are absorbed by the solvent and are extracted from the kettle. Light components such as methane, oxygen, and CO with a small amount of the absorbent are extracted from the top of the tower.

(5) Desorption: the theoretical plate number of the desorption towers is 30, and the operating pressure is 2.2 MPa. After desorption, the gas from the top of the desorption tower is sent to the deethanizer, and the lean solvent from the kettle is heat exchanged stepwise and cooled to −35° C., and then sent back to the absorption tower for recycling.

(6) Deethanization: the theoretical plate number of the deethanizer is 50, and the operating pressure is 2.0 MPa. C2 component rich in ethylene and ethane is extracted from the top of the deethanizer, and C3 component rich in propylene and propane is extracted from the kettle of the deethanizer.

(7) Ethylene rectification: the theoretical plate number of the ethylene rectifying tower is 90, and the operating pressure is 2.0 MPa. The gas from the top of the deethanizer is sent to the C2 hydrogenation reactor to remove the alkyne and then sent to the ethylene rectifying tower. The gas from the top of the ethylene rectifying tower is sent back to the four-stage inlet of the compressor, the ethylene product is obtained on the side, and the ethane-rich product is obtained from the kettle and sent to the cracking furnace.

(8) Depropanization: the theoretical plate number of the depropanizer is 40, and the operating pressure is 0.7 MPa. The material from the top of the depropanizer is sent to the C3 hydrogenation reactor to remove alkyne and alkadiene, and the material from the kettle of the depropanizer is obtained as C4 product and sent to the cracking furnace.

(9) Propylene rectification: the material from the C3 hydrogenation reactor is fed into the propylene rectifying tower. The theoretical plate number of the propylene rectifying tower is 160, the operating pressure is 1.7 MPa. The gas phase from the top of the propylene rectifying tower is sent back to the four-stage inlet of the compressor, propylene product is obtained on the side, and the main material from the kettle is propane-rich product, which is sent to the cracking furnace.

(10) Cracking: the ethane-rich product obtained in step (7), the C4-rich product obtained in step (8), and the propane-rich product obtained in step (9) are fed into the cracking furnace. The resulting cracked gas is subjected to heat recovery in the waste heat boiler, cooled in the oil washing tower/water washing tower, and then fed into the first suction tank of the compressor.

(11) Cold energy recovery: the unabsorbed gas from the top of the absorption tower is fed into the cold box to reduce the temperature to −45° C., and then fed into the flash tank for flash evaporation. The liquid from the bottom of the flash tank is sent back to the top of the absorption tower, and the exhaust gas rich in components such as methane, oxygen, CO is fed into the cold box, pressurized in a booster driven by the expander and then discharged.

The composition of the resulting ethylene product is shown in Table 10, and the yield of the ethylene product is shown in Table 12.

TABLE 10

| Composition | mol % |
| --- | --- |
| methane | 0.03 |
| ethylene | 99.95 |
| ethane | 0.02 |

The composition of the resulting propylene product is shown in Table 11.

TABLE 11

| Composition | mol % |
| --- | --- |
| propylene | 95.2 |
| propane | 4.8 |

In Example 4, the amount of the absorbent to be supplemented is 2887 Kg/h, and the ethylene recovery rate was 99.9%.

Comparative Example 2

The differences from Example 4 only are that a cracking furnace is not arranged, and the ethane-rich product obtained in step (7), the C4-rich product obtained in step (8), and the propane-rich product obtained in step (9) are discharged beside the boundary area.

In Comparative Example 2, the amount of the absorbent to be supplemented is 3654 Kg/h.

Compared with Comparative Example 2, the amount of the absorbent to be supplemented in Example 4 is reduced by 21%.

TABLE 12

| Example | Ethylene product kg/h | Ethylene product obtained without circulation of saturated hydrocarbon kg/h | Ethylene increase rate % |
| --- | --- | --- | --- |
| 1 | 17625.14 | 13297.60 | 0.33 |
| 2 | 19256.14 | 13273.68 | 0.45 |
| 3 | 29319.82 | 13328.44 | 1.20 |
| 4 | 18384.55 | 13317.45 | 0.38 |

It should be noted that the above-mentioned examples are only used to explain the present invention, and do not constitute any limitation to the present invention. The present invention may be modified within the scope as specified by the claims of the present invention, and the present invention may be modified without departing from the scope and spirit of the present invention. Although the present invention described therein relates to specific methods, materials, and examples, it does not mean that the present invention is limited to the specific examples disclosed therein. On the contrary, the present invention can be extended to all other methods and applications having the same functions.

The invention claimed is:

1. A method for separating light hydrocarbons, comprising the following steps:
    (1) compressing and cooling C1-C4 hydrocarbon-containing hydrocarbon material to be separated to produce compressed and cooled hydrocarbon material, wherein the C1-C4 hydrocarbon-containing hydrocarbon material contains at least one olefin selected from C2-C4 olefins and at least one alkane selected from C1-C4 alkanes;
    (2) contacting the compressed and cooled hydrocarbon material with an absorbent to absorb hydrocarbons with two or more carbon atoms to produce a solvent-rich material;
    (3) rectifying the solvent-rich material to produce a gas-phase material containing olefins and saturated alkanes and a solvent-lean material;
    (4) rectifying the gas-phase material containing olefins and saturated alkanes one or more times to produce one or more streams of a saturated-alkane-rich liquid-phase material;
    (5) cracking the one or more streams of the saturated-alkane-rich liquid-phase material to produce a cracked gas; and
    (6) circulating the cracked gas to the step (1);
    wherein the step (4) comprises:
    feeding the gas-phase material containing olefins and saturated alkanes into a second rectifying tower for rectification, obtaining a first stream containing ethane and ethylene from the top part of the second rectifying tower and a second stream containing hydrocarbons with three or more carbon atoms from the bottom; feeding the first stream into a third rectifying tower for rectification, obtaining an ethylene product stream on the side part, a third stream containing ethylene from the top part of the third rectifying tower, and an ethane-rich fourth stream from the bottom.

2. The method according to claim 1, wherein in the step (6), the circulating the cracked gas to the step (1) comprises: combining the cracked gas with the C1-C4 hydrocarbon-containing hydrocarbon material to be separated and then compressing and cooling; or compressing the cracked gas, combining the compressed cracked gas with the compressed C1-C4 hydrocarbon-containing hydrocarbon material, and cooling; or compressing and cooling the cracked gas, and combining the compressed and cooled cracked gas with the compressed and cooled C1-C4 hydrocarbon-containing hydrocarbon material.

3. The method according to claim 1, wherein the at least one olefin is selected from ethylene, propylene, 1-butene, 2-butene, and 1,3-butadiene; and/or the at least one alkane is selected from methane, ethane, propane, n-propane, iso-propane, n-butane, tert-butane and iso-butane; and/or the saturated alkane is selected from one or more of ethane, propane, n-butane, and iso-butane.

4. The method according to claim 1, wherein the absorbent is selected from a C3 fraction containing C3 alkane, a C4 fraction containing C4 alkane, and a C5 fraction containing C5 alkane.

5. The method according to claim 4, wherein the C3 alkane is n-propane, and/or the C4 alkane is n-butane, and/or the C5 alkane is selected from n-pentane and isopentane.

6. The method according to claim 1, wherein the temperature of the cracking is in a range of 500-850° C.

7. The method according to claim 1, wherein in the step (1), the C1-C4 hydrocarbon-containing hydrocarbon material is compressed to a pressure in a range of 2.0-5.0 MPa; and/or the C1-C4 hydrocarbon-containing hydrocarbon material is cooled to a temperature in a range of −40° C.

8. The method according to claim 1, wherein the C1-C4 hydrocarbon-containing hydrocarbon material is one or more selected from reaction gas of oxidation of methane to ethylene, refinery dry gas, dry gas of chemical processing of coal, catalytically cracked products, Fischer-Tropsch exhaust gas, propane dehydrogenated product, separated methane gas, and separated shale gas.

9. The method according to claim 1, wherein the step (2) comprises: contacting the compressed and cooled hydrocarbon material with the absorbent in a first absorption tower, obtaining a gas-phase stream containing light components from the top part of the tower and the solvent-rich material from the bottom.

10. The method according to claim 9, comprising feeding the gas-phase stream containing light components from the top part of the first absorption tower into a second absorption tower to contact with a re-absorbent therein, so as to absorb an entrained absorbent and C2 hydrocarbon that is not absorbed by the absorbent in the first absorption tower.

11. The method according to claim 10, wherein an exhaust gas obtained from the top part of the second absorption tower is discharged outside a boundary area, and a liquid-phase material obtained from the bottom is discharged outside the boundary area or subjected to other treatments.

12. The method according to claim 11, wherein the other treatments include: feeding the liquid-phase material obtained from the second absorption tower into a sixth rectifying tower for rectification, feeding a gas-phase stream obtained from the top of the sixth rectifying tower into the first absorption tower as a circulating absorbent, feeding a liquid-phase stream obtained from the bottom into the second absorption tower as a circulating re-absorbent.

13. The method according to claim 9, comprising subjecting the gas-phase stream containing light components from the top part of the first absorption tower to cold energy recovery.

14. The method according to claim 13, comprising cooling the gas-phase stream containing light components through a cold box, expanding and flashing to recover unabsorbed C2 hydrocarbons and an entrained absorbent, pressurizing an exhaust gas without C2 hydrocarbons by a booster driven by an expander, and discharging.

15. The method according to claim 13, comprising feeding the gas-phase stream containing light components into a cold box to be cooled to a temperature in a range of −80° C. to −35° C., expanding the gas by an expander and feeding into a flash tank for flash evaporation, feeding the gas from the top part of the flash tank into the cold box and then boosting in a booster driven by the expander and discharging, sending a liquid from the bottom part of the flash tank back to the top part of the first absorption tower.

16. The method according to claim 9, wherein the theoretical plate number of the first absorption tower is in a range of 30-80, and the operating pressure is in a range of 2.0-6.0 MPa.

17. The method according to claim 1, wherein the step (3) comprises feeding the solvent-rich material from the step (2) into a first rectifying tower for rectification, obtaining the gas-phase material containing olefins and saturated alkanes from the top part of the first rectifying tower and the solvent lean material from the bottom.

18. The method according to claim 17, comprising feeding the solvent-lean material into a first absorption tower as a circulating absorbent.

19. The method according to claim 1, wherein before being fed into the third rectifying tower, feeding the first streatm into a first hydrogenation reactor for selective hydrogenation to remove alkyne and/or alkadiene.

20. The method according to claim 19, wherein the step (4) further comprises:

rectifying the second stream in a fourth rectifying tower, obtaining a fifth stream containing propane and propylene from the top part of the tower and a saturated alkane-rich sixth stream from the bottom.

21. The method according to claim 20, wherein the step (4) further comprises:

feeding the fifth stream into a fifth rectifying tower for rectification, obtaining a stream of propylene product on the side part, a seventh stream containing propylene from the top part of the tower, and a propane-rich eighth stream from the bottom;

optionally, before being fed into the fifth rectifying tower, feeding the fifth stream into a second hydrogenation reactor for selective hydrogenation to remove alkyne and/or alkadiene;

optionally, circulating part or all of the seventh stream to the step (1).

22. The method according to claim 21, comprising cracking one or more of the fourth stream, the sixth stream, and the eighth stream to produce cracked gas.

23. The method according to claim 20, comprising cracking one or more of the fourth stream and the sixth stream to produce cracked gas.

24. The method according to claim 19, wherein the step (4) further comprises:
rectifying the second stream in a fifth rectifying tower, obtaining a stream of propylene product on the side part, a ninth stream containing propylene from the top part of the tower, and a saturated alkane-rich tenth stream from the bottom;
optionally, circulating part or all of the ninth stream to the step (1);
optionally, before being fed into the fifth rectifying tower, feeding the second stream into a third hydrogenation reactor for selective hydrogenation to remove alkyne and/or alkadiene.

25. The method according to claim 1, comprising subjecting the cracked gas to heat recovery in a waste heat boiler and feeding into an oil washing tower and/or a water washing tower, and then circulating to the step (1) for compression.

26. A system for separating light hydrocarbons, comprising:
a compressing and cooling unit, an absorption unit, a desorption unit, a rectifying unit, and a cracking unit, wherein the absorption unit is connected to the compressing and cooling unit and the desorption unit, respectively, the rectifying unit is connected to the desorption unit and the cracking unit, respectively, and the cracking unit is connected to the compressing and cooling unit;
wherein the compressing and cooling unit comprises a compressor and a heat exchanger, the absorption unit comprises a first absorption tower, the desorption unit comprises a first rectifying tower, the rectifying unit comprises a second rectifying tower and a third rectifying tower, and the cracking unit comprises a cracking furnace.

27. The system according to claim 26, wherein an outlet of the compressor is connected to an inlet of the heat exchanger, an outlet of the heat exchanger is connected to a first inlet of the first absorption tower, a bottom outlet of the first absorption tower is connected to an inlet of the first rectifying tower, and a top outlet of the first rectifying tower is connected to an inlet of the second rectifying tower.

28. The system according to claim 26, wherein a top outlet of the second rectifying tower is connected to an inlet of the third rectifying tower, and a bottom outlet of the third rectifying tower is connected to a first inlet of the cracking furnace; optionally, a first hydrogenation reactor is arranged between the top part of the second rectifying tower and the third rectifying tower; optionally, a top outlet of the third rectifying tower is connected to an inlet of the compressor.

29. The system according to claim 26, wherein the rectifying unit further comprises a fourth rectifying tower, wherein an inlet of the fourth rectifying tower is connected to a bottom outlet of the second rectifying tower, and a bottom outlet of the fourth rectifying tower is connected to a first inlet and/or a second inlet of the cracking furnace.

30. The system according to claim 29, wherein the rectifying unit further comprises a fifth rectifying tower, wherein a top outlet of the fourth rectifying tower is connected to the fifth rectifying tower, a second hydrogenation reactor is optionally arranged between the fifth rectifying tower and the fourth rectifying tower, a bottom outlet of the fifth rectifying tower is connected to the first inlet and/or the second inlet and/or a third inlet of the cracking furnace, and optionally, a top outlet of the fifth rectifying tower is connected to a first inlet of the compressor.

31. The system according to claim 26, wherein the cracking unit further comprises a waste heat boiler and an oil washing tower and/or water washing tower, wherein an outlet of the cracking furnace is connected to an inlet of the waste heat boiler, an outlet of the waste heat boiler is connected to an inlet of the oil washing tower and/or water washing tower, and an outlet of the oil washing tower and/or water washing tower is connected to a first inlet and/or a second inlet of the compressor.

32. The system according to claim 26, wherein a bottom outlet of the first absorption tower is connected to an inlet of the first rectifying tower, a top outlet of the first absorption tower is connected to a first inlet of a second absorption tower, and a bottom outlet of the second absorption tower is optionally connected to an inlet of a sixth rectifying tower.

33. The system according to claim 32, wherein a top outlet of the sixth rectifying tower is connected to a second inlet of the first absorption tower, and a bottom outlet of the sixth rectifying tower is connected to a second inlet of the second absorption tower.

34. The system according to claim 26, wherein a bottom outlet of the first absorption tower is connected to an inlet of the first rectifying tower, and a top outlet of the first absorption tower is connected to a cold energy recovery unit.

35. The system according to claim 34, wherein the cold energy recovery unit comprises a cold box, an expander, a flash tank and a booster, wherein a first inlet of the cold box is connected to the top outlet of the first absorption tower, a first outlet of the cold box is connected to an inlet of the expander, an outlet of the expander is connected to an inlet of the flash tank, a first outlet of the flash tank is connected to a second inlet of the cold box, a second outlet of the cold box is connected to an inlet of the booster, and optionally a second outlet of the flash tank is connected to a second inlet of the first absorption tower.

36. The system according to claim 26, wherein the system further comprises a purification device arranged between the first rectifying tower and the second rectifying tower, for removing acid gas and/or moisture from the material from the top part of the first rectifying tower; or the system further comprises a purification device arranged between the compressor and the heat exchanger, for removing acid gas and/or moisture from the material from the compressor.

* * * * *

UNITED STATES PATENT AND TRADEMARK OFFICE
CERTIFICATE OF CORRECTION

| | |
|---|---|
| PATENT NO. | : 11,649,406 B2 |
| APPLICATION NO. | : 17/283606 |
| DATED | : May 16, 2023 |
| INVENTOR(S) | : Shujuan Luo et al. |

It is certified that error appears in the above-identified patent and that said Letters Patent is hereby corrected as shown below:

In the Claims

Claim 14, Column 20, Line 12, "andflashing" should read as --and flashing--.

Claim 19, Column 20, Line 41, "streatm" should read as --stream--.

Signed and Sealed this
Fifth Day of September, 2023

Katherine Kelly Vidal
*Director of the United States Patent and Trademark Office*